(12) United States Patent
Rusch

(10) Patent No.: US 8,702,764 B2
(45) Date of Patent: Apr. 22, 2014

(54) FASTENING APPARATUS FOR SURGICAL RETAINING SYSTEMS

(75) Inventor: Christoph Rusch, Biel (CH)

(73) Assignee: Creaholic S.A., Biel (CH)

(*) Notice: Subject to any disclaimer, the term of this patent is extended or adjusted under 35 U.S.C. 154(b) by 80 days.

(21) Appl. No.: 13/264,310

(22) PCT Filed: Apr. 19, 2010

(86) PCT No.: PCT/CH2010/000105
§ 371 (c)(1),
(2), (4) Date: Nov. 1, 2011

(87) PCT Pub. No.: WO2010/121388
PCT Pub. Date: Oct. 28, 2010

(65) Prior Publication Data
US 2012/0053638 A1    Mar. 1, 2012

(30) Foreign Application Priority Data
Apr. 20, 2009   (CH) .................................. 619/09

(51) Int. Cl.
*A61B 17/68* (2006.01)
*A61B 17/80* (2006.01)
*A61B 17/84* (2006.01)

(52) U.S. Cl.
USPC .......................................... 606/289; 606/290

(58) Field of Classification Search
USPC ........................................ 606/287–290, 293
See application file for complete search history.

(56) References Cited

U.S. PATENT DOCUMENTS

| | | | |
|---|---|---|---|
| 5,531,746 A * | 7/1996 | Errico et al. .................. 606/287 |
| 2003/0187442 A1* | 10/2003 | Richelsoph et al. ............ 606/70 |
| 2004/0073218 A1* | 4/2004 | Dahners .......................... 606/69 |
| 2004/0122426 A1 | 6/2004 | Michelson | |
| 2005/0149027 A1 | 7/2005 | Campbell et al. | |
| 2006/0241618 A1* | 10/2006 | Gasser et al. ................... 606/72 |

FOREIGN PATENT DOCUMENTS

| | | |
|---|---|---|
| EP | 0988833 | 3/2000 |
| EP | 1346697 | 9/2003 |
| FR | 2792185 | 10/2000 |

* cited by examiner

*Primary Examiner* — Christian Sevilla
(74) *Attorney, Agent, or Firm* — Rankin, Hill & Clark LLP

(57) ABSTRACT

A fastening apparatus for surgical retaining systems includes at least one retaining element and a fastening element, which are mechanically connected to each other. A joint socket of the retaining element and a correspondingly shaped joint head of the fastening element form a ball-and-socket joint. A movement of the ball-and-socket joint can be locked by turning an eccentrically shaped clamping element.

11 Claims, 3 Drawing Sheets

FASTENING APPARATUS FOR SURGICAL RETAINING SYSTEMS

BACKGROUND OF THE INVENTION

1. Field of the Invention

The invention relates to the field of surgical retaining systems and in particular to a fastening apparatus for surgical retaining systems, a surgical retaining element, a fastening element, and a fastening method for surgical retaining systems, according to the preamble of the corresponding independent claims.

2. Description of Related Art

Surgical retaining systems, for example for fixing broken bones, often consist of plates that are secured by screws in the bone. The plates comprise openings into which the screws are introduced at different angles. While the screws are being screwed into the bone, the screws can be fixed in the plate, for example by a thread on the screw head, which thread cuts into the plate.

A disadvantage of this design is that the retaining systems may be deformed after the screws have been tightened, and the position of a plate can no longer be corrected by the already secured screws. Readjustment of the plate, by loosening and retightening the screws, in some cases requires replacement of the fastening screws and/or of the plate. A further disadvantage is that the screws press the plate against the bone. This can cause the bone to give way and can thus lead to a loose connection.

BRIEF SUMMARY OF THE INVENTION

The object of the invention is therefore to make available a fastening apparatus for surgical retaining systems, a surgical retaining element, a fastening element, and a fastening method for surgical retaining systems, of the kind mentioned at the outset, that remedy the abovementioned disadvantages.

This object is achieved by a fastening apparatus for surgical retaining systems, a surgical retaining element, a fastening element, and a fastening method for surgical retaining systems, with the features of the corresponding independent claims.

The fastening apparatus, provided for surgical retaining systems, comprises at least one retaining element and one fastening element, which can be mechanically connected to each other. The retaining element comprises a joint socket, and the fastening element comprises a joint head. The joint socket and the joint head preferably correspond at least partially in shape to each other and together form a ball-and-socket joint. The movement of the ball-and-socket joint can be locked by means of a clamping element.

The ball-and-socket joint can be obtained by means of the joint head and the joint socket both having spherical surfaces completely matching each other. In a second preferred embodiment of the invention, the joint socket is spherical only in a partial area and, in a remaining area, is designed opening preferably conically toward the clamping element. The partial area in this case lies on that side of the retaining element directed away from the clamping element, and the remaining area lies between the partial area and the clamping element. In a third preferred embodiment of the invention, the joint socket is designed opening completely, preferably conically, toward the clamping element. In the second and third embodiments of the invention too, the spherical shape of the joint head means that a ball-and-socket joint connection is formed with the joint socket.

It is thus possible to adjust the position of a surgical plate or of a retaining element, even when one or more fastening elements are already connected firmly to a substrate, for example to a bone. This is achieved by the positioning of the retaining element being released and then locked again by the clamping element. It is also possible to screw the screws into the bone at an angle that can be chosen relatively freely, and, independently of the exact position of the screws, to lock them to the plate at a stable angle. It is not necessary here for the screw to press the plate against the bone.

A further advantage is that the fastening element can be locked with respect to the retaining element independently of whether the retaining element is pressed against the substrate or not. Thus, for example, with the clamping element loosened, it is possible to draw a bone to a greater or lesser extent toward the retaining element by turning a fastening element provided with a screw thread. This may be necessary in order to position the bone at a predefined distance from the retaining element, or in order to retighten the connection after a period of time. Thus, in contrast to the prior art, where the screw is locked only when the screw presses against a plate as retaining element, the invention affords greater freedom in terms of the positioning of the retaining element.

The ball-and-socket joint of the fastening apparatus, in the locked state by means of the clamping element, does not allow any translational movement of the joint head with respect to the joint socket. In particular, therefore, the retaining element is not movable along the fastening element, as would be the case in a simple screw. For this purpose, the joint socket preferably encloses the joint head of the fastening element at least partially and centers the joint head or the center of the ball inside the retaining element. In this case, the joint head is preferably almost fully recessible within the retaining element.

The clamping element of the fastening apparatus preferably comprises an eccentrically shaped ring which, when the ring is turned, clamps and/or braces the joint head with respect to the joint socket. An inner surface and outer surface of the ring have a rotationally symmetrical shape, wherein the inner surface and outer surface of the ring preferably extend eccentrically to each other and, as a result, the axes of the inner and outer ring surfaces do not overlap or do not coincide.

The retaining element preferably comprises a circumferential groove, in particular an annular groove, which adjoins the joint socket. The inner surface of the circumferential groove preferably extends rotationally symmetrically, but eccentrically with respect to the joint socket, and is shaped corresponding to the outer surface of the clamping element or ring. By means of the eccentric shape of the annular groove and of the ring, it is possible to clamp the joint head in the joint socket by turning the ring.

The clamping element is provided with a contact surface, which preferably has a geometry corresponding to the joint head. When the clamping element is turned, the contact surface presses against the spherical-portion-shaped outer surface of the joint head. The outer side of the clamping element preferably comprises a flange and/or a cone that corresponds to the shape of the annular groove. The clamping element preferably comprises one or more guides, which are suitable for the engagement of a tool, in order to perform a clamping movement.

In a preferred embodiment of the invention, the clamping element comprises an opening, which allows the clamping element to be compressed in the direction of the diameter thereof. This opening can at the same time also serve as a guide for the tool. A further guide in the fastening element is, for example, a U-shaped cutout. This additionally provides a flexurally weak point that makes the clamping element bendable. This flexurally weak point allows the clamping element to be more easily pressed into the annular groove provided for this purpose on the retaining element.

In another preferred embodiment, the clamping element comprises cams for a bayonet catch, which cams protrude in the radial direction. Correspondingly, indents in the shape of radial slits are then formed on the retaining element, said indents being provided for the insertion of the cams of the clamping element. The connection between the clamping element and the retaining element can thus be made by a push-in and turn movement, without the clamping element having to be compressed.

The contact surface of the clamping element corresponds at least approximately to a portion of the geometry of a joint head, wherein the contact surface of the clamping element and/or the joint socket and/or the joint head preferably comprises one or more fixing elements that protrude from the remaining area of the contact surface. When the clamping element is turned, these fixing elements can cut into the corresponding part. The fixing elements can, for example, comprise one or more cutting edges, which run circumferentially and parallel to the plane of the clamping element and which can themselves in turn comprise several individual portions. The fixing elements can also be formed microscopically, by one or more of the mutually contacting surfaces on the clamping element and/or joint socket and/or joint head being roughened. In a preferred embodiment of the invention, the fixing elements are formed on the joint socket and/or on a lower part of the joint head that can be pressed against the joint socket. This prevents the joint head from also turning too when the clamping element is being tightened.

The fastening element preferably comprises a shank, which can optionally have a thread or another form-fit connection or force-fit connection. In other embodiments of the invention, the shank is provided for a materially cohesive connection. The joint head of the fastening element is preferably provided with a recess for a tool. In a preferred embodiment of the subject matter of the invention, the recess of the fastening element is shaped in such a way that a tool can be introduced into the recess at what is, within limits, a freely movable angle to the longitudinal axis of the fastening element. An axis of rotation of the fastening element preferably extends through the center of the joint head.

One or more joint sockets with corresponding annular grooves are formed on the surgical retaining element. The retaining element can already be equipped with one or more rings before the connection to a fastening element.

In the fastening method, the fastening element is preferably inserted into the joint socket of the retaining element, where the rings or clamping elements are already pre-installed, for example. After roughly orienting the retaining element to the desired position, the fastening elements are screwed, preferably all the way through the retaining element, into the substrate, for example a bone. The clamping elements are not yet in the locked state, such that the retaining element, in its orientation to the substrate, can be positioned free of tension. The fastening elements are locked onto the retaining element by rotation of the clamping elements by means of a tool. Recorrections can be made by releasing one or more clamping elements. The clamping element can be held in its position by means of a tubular wrench during the installation of the fastening element and also during the fastening or subsequent adjustment of the fastening element, and in this way it can be secured against turning with the fastening element. This prevents undesired jamming of the clamping element.

In principle, the described fastening apparatus can also be used in other applications, for example in machine constructions, for holders and stands and the like.

Other preferred embodiments are set forth in the dependent claims. Features of the method claims can by analogy, be combined with the device claims, and vice versa.

BRIEF DESCRIPTION OF THE DRAWINGS

The subject matter of the invention is explained in more detail below on the basis of preferred illustrative embodiments depicted schematically in the attached drawings, in which.

The reference signs used in the drawings are set out, together with their respective meanings, in the list of reference signs. Identical parts in the figures are in principle provided with the same reference signs.

DETAILED DESCRIPTION OF THE INVENTION

Figure 1:
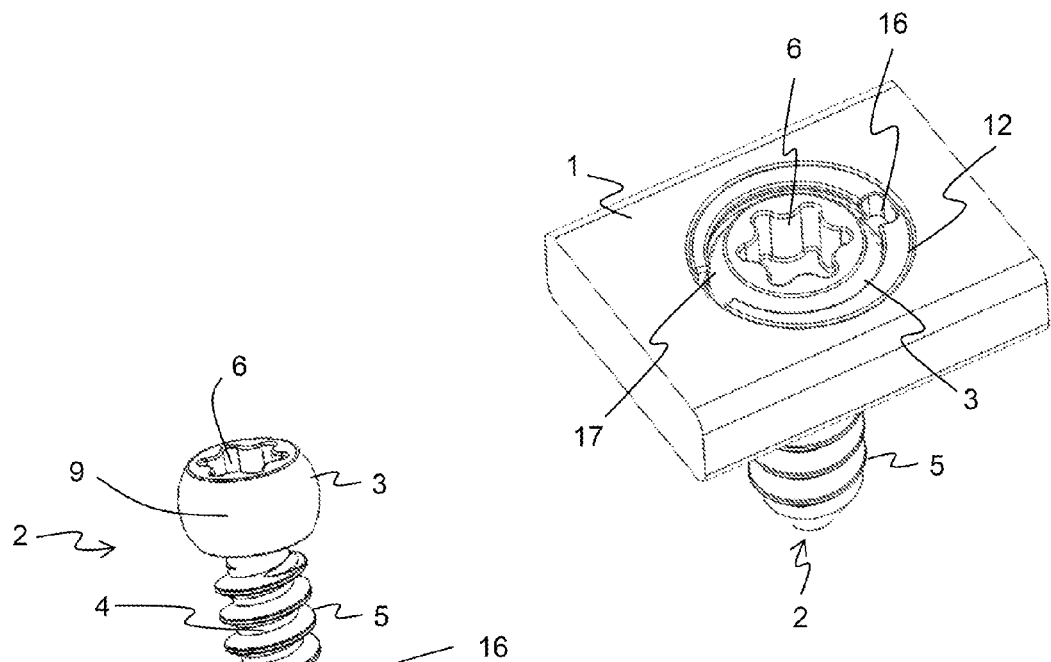
FIG. 1 shows a fastening apparatus in an unlocked state.

FIG. 1 shows a fastening apparatus with a retaining element 1, a fastening element 2 and a clamping element 12, in the unlocked state.

Figure 2:
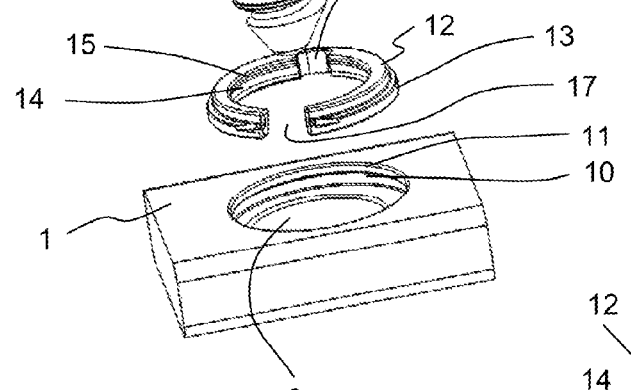
FIG. 2 shows an exploded view of the fastening apparatus.

FIG. 2 shows the various elements in an exploded view. The fastening element 2 with a joint head 3 is placed in a retaining element 1, which comprises a recess for the fastening element 2 with a joint socket 8. The fastening element 2 has a recess 6 for a socket wrench, and it also has a shank 4. The shank 4 is provided, for example, with a thread 5 and can be screwed into a substrate that is to be fixed or stabilized, for example into a bone. By means of the ball-and-socket joint composed of joint socket 8 and joint head 3, the fastening element 2 is movable in the retaining element 1. However, the retaining element 1 is not movable in translation along the fastening element 2. The ball-and-socket joint can be secured or fixed by a clamping element or a ring 12. The ring has an opening 17 and a flexurally weak point 16, which are provided for easier mounting of the ring 12 into a circumferential annular groove 10 of the retaining element 1.

Figure 3:
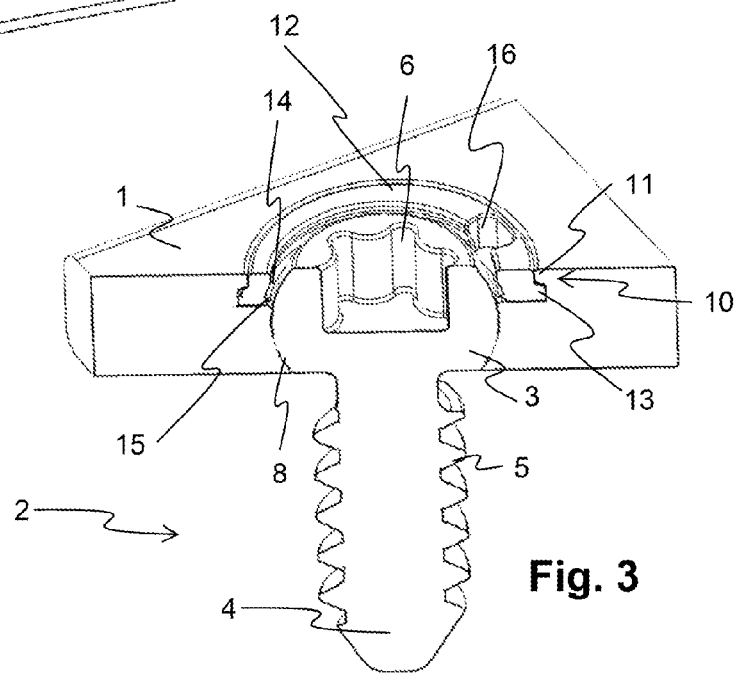
FIG. 3 shows a section through the fastening apparatus in the unlocked state.

FIG. 3 shows a section through the fastening apparatus with retaining element 1, fastening element 2 and ring 12 in the unlocked state. In this state, an inner surface or contact surface 14 of the ring 12 lies at least approximately symmetrical with respect to the center of the joint head 3. The annular groove 10 is arranged eccentrically with respect to the center of the joint head 3 and, if appropriate, also with respect to a longitudinal axis of the fastening element 2. In the position of the ring 12 as shown, the fastening element 2 and the retaining element 1 can move relative to each other about the ball-and-socket joint.

The opening 17 on the clamping element 12 permits widening and compressing of the ring 12. In this way, the clamping element 12 can be compressed and fitted into the annular groove 10. The clamping element 12 is secured against springing out by a flange 13 on the ring and by a matching shoulder 11 on the annular groove 10. Instead of the flange or in addition thereto, the ring and annular groove can also have a mutually corresponding conical configuration.

In the area of the contact surface 14, there are one or more fixing elements 15, roughened structures or macroscopic elevations, which are provided for locking the joint head 3. The fixing element 15 in this figure is not in engagement with the joint head 3. The fastening element 2 is provided with a recess for a tool, for example a socket wrench. The fixing elements can also be formed on the joint socket 8 or on the joint head 3.

When the clamping element 12 is turned, the center of the inner surface 14 of the clamping element 12 shifts and thus locks the joint head 3 of the fastening element 2 with respect to the joint socket 8. The fixing elements 15 cut into the joint head 3 and thereby provide additional locking against possible loosening of the connection 2.

The dimensions, in particular internal diameter and external diameter, of the clamping element 12 are preferably chosen such that, on the one hand, the clamping element can be fitted into the annular groove 10 by being compressed and, on the other hand, the clamping element 12 can be widened to such an extent that the joint head 3 can be guided through the clamping element 12.

Figure 4:
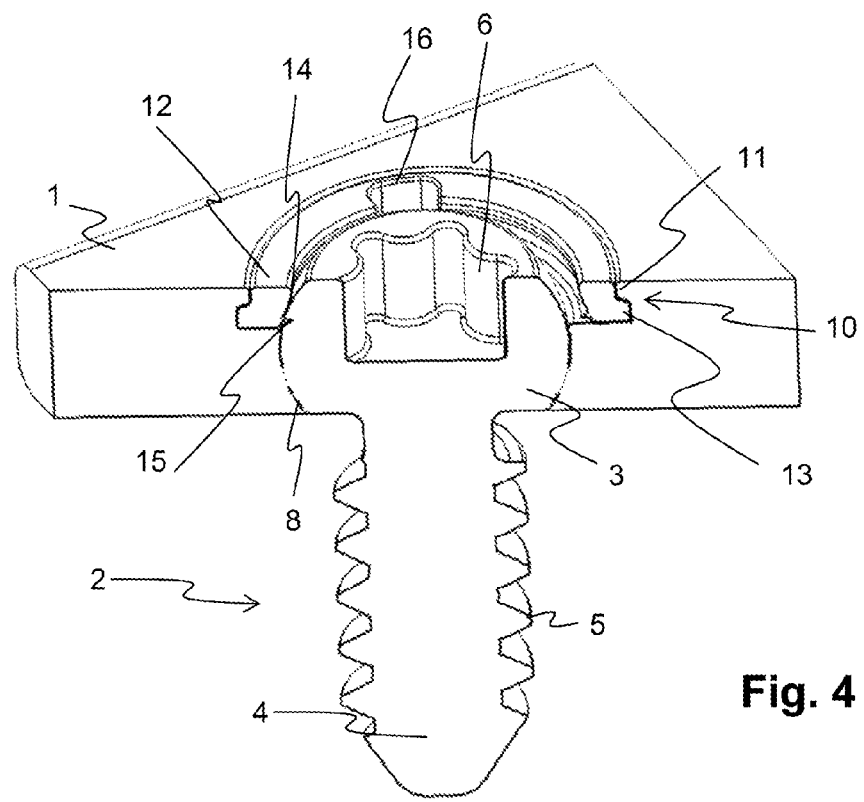
FIG. 4 shows a section through the fastening apparatus in a locked state.

FIG. 4 shows a section through the fastening apparatus in the locked state. The fastening element 2 with the shank 4 and the joint head 3 is still positioned coaxially with respect to the joint socket 8 of the retaining element 1. The eccentric arrangement of the contact surface 14 of the ring 12 with respect to the outer surface of the ring 12 and the annular groove 10 of the retaining element 1 has the effect that the fastening element 2 is locked in the joint socket 8 relative to the retaining element 1 when the clamping element 12 is turned. The optional fixing elements 15 cut into the joint head 3 of the fastening element 2 as a result of the eccentric positioning.

Figure 5:
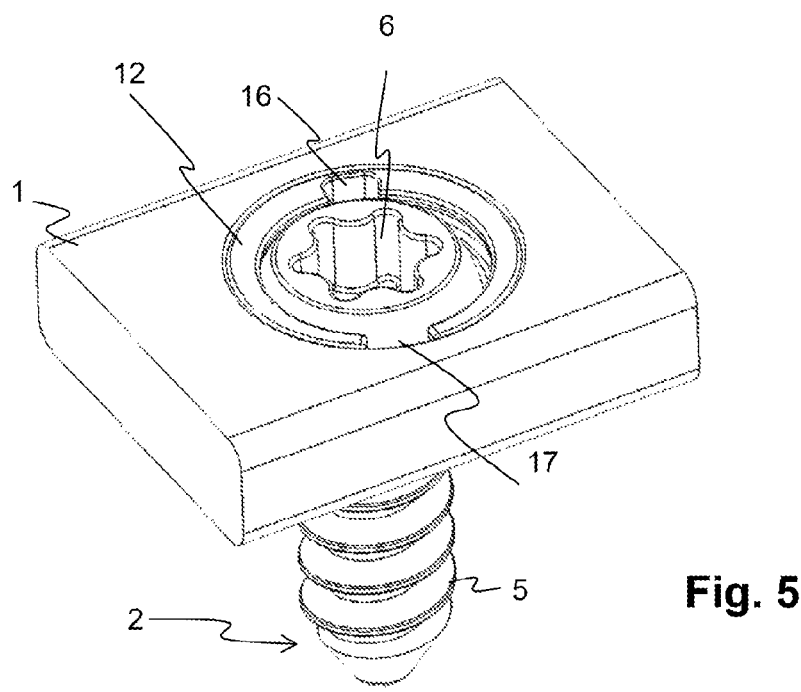
FIG. 5 shows the fastening apparatus in a locked state.

FIG. 5 likewise shows the fastening apparatus in the locked state. In this depiction, the clamping element 12 has been turned counterclockwise through ca. 60° in relation to FIG. 1 and FIG. 2. When turned clockwise, the clamping element 12 is again brought to its neutral position and thus releases the locking of the fastening element 2 relative to the retaining element 1. In this way, the orientation of the retaining element 1 with respect to the fastening element 2 can be corrected.

Figure 6:
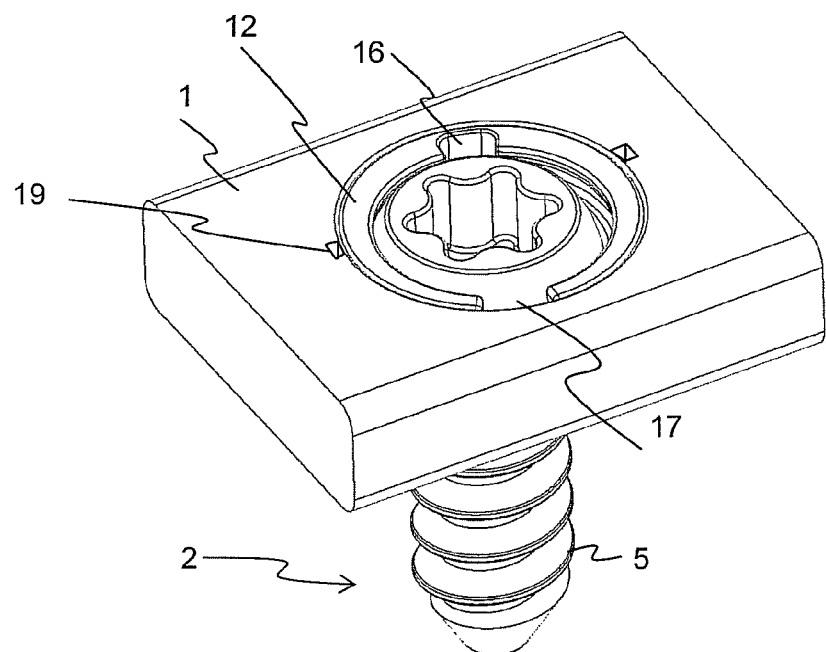
FIG. 6 shows a fastening apparatus in a locked state in another embodiment.

FIG. 6 shows another embodiment of a fastening apparatus, of which the clamping element 12 is held in the manner of a bayonet catch in the annular groove 10. For this purpose, indents 19 are arranged on the periphery of the annular groove 10 and receive corresponding projections of the ring 12. A flange 13 and a shoulder 11 or a cone are not necessary for this embodiment.

Figure 7:
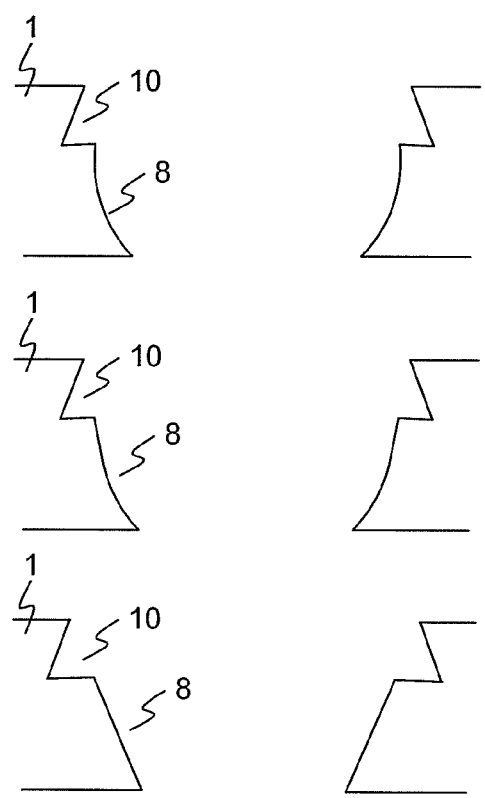
FIG. 7 shows different shapes of joint sockets.

FIG. 7 shows schematically, in each case in cross section through a retaining element 1, different shapes of joint sockets 8, specifically from top to bottom:
- a spherical joint socket;
- a joint socket 8 with a conical area adjoining the annular groove 10 and, adjoining said conical area, a spherical area;
- a joint socket 8 with a conical area adjoining the annular groove 10 and extending as far as the opposite side of the retaining element.

The two lower shapes, that is to say with a joint socket 8 opening toward the annular groove 10, permit insertion of the fastening element 2 in a direction that deviates from the normal with respect to the orientation of the retaining element 1. Although the annular groove is depicted conically here, it can of course also be stepped here (that is to say with a shoulder 11) or can be conical/stepped in combination.

FIGS. 1-7 each show details of a surgical retaining element 1. A complete surgical retaining element 1 preferably comprises several recesses for fastening elements 2. In applications on the spinal column, embodiments with just one joint could also be used.

The invention claimed is:

1. A fastening apparatus for surgical retaining systems, comprising:
a retaining element, a fastening element, and a clamping element that are adapted to be mechanically connected to each other,
wherein the retaining element comprises a joint socket and the fastening element comprises a joint head,
wherein the joint socket and the joint head are shaped corresponding to each other and form a ball-and-socket joint,
wherein movement of the ball-and-socket joint is lockable by engagement with the clamping element,
wherein the clamping element is an eccentric ring and comprises a contact surface that is adapted to be pressed against a ball surface of the joint head to provide wedging engagement therewith, and wherein the clamping element is rotatably arranged relative to the retaining element whereby the clamping element, when rotated, wedges the joint head with respect to the joint socket,
wherein the eccentric ring is a split ring having a center of an inner circumference being offset from a center of an outer circumference, and
wherein the clamping element is arranged rotatably in a mount in the retaining element, this mount formed by an eccentric groove retaining the clamping element within the retaining element, the eccentric groove having a center of an inner circumference being offset from a center of an outer circumference.

2. The fastening apparatus as claimed in claim 1, wherein the ball-and-socket joint, in a locked state, does not allow any translational movement of the joint head with respect to the joint socket.

3. The fastening apparatus as claimed in claim 1, wherein the contact surface is provided on an inner side of the clamping element.

4. The fastening apparatus as claimed in claim 3, wherein the contact surface at least approximately forms a portion of a ball surface.

5. The fastening apparatus as claimed in claim 3, wherein the contact surface and/or the joint socket comprises at least one fixing element, which protrudes from an area of the contact surface and/or of the joint socket and can be pressed against the joint head by turning the clamping element.

6. The fastening apparatus as claimed in claim 5, wherein the at least one fixing element is formed by one or more cutting edges running circumferentially and at least approximately parallel to a plane of the clamping element.

7. The fastening apparatus as claimed in claim 1, wherein the clamping element, on its outer side, has a flange, a shape of which corresponds to a shape of a shoulder on an inner side of the eccentric groove.

8. The fastening apparatus as claimed in claim 1, wherein the clamping element forms, on its outer side, an external cone, and an inner side of the eccentric groove forms an internal cone.

9. The fastening apparatus as claimed in claim 1, wherein the clamping element has an opening, which provides an engagement possibility for a tool for turning the clamping element.

10. The fastening apparatus as claimed in claim 1, wherein the clamping element and the eccentric groove form a bayonet catch.

11. The fastening apparatus as claimed in claim 1, wherein the fastening element comprises a shank, which is secured to the joint head and has a thread.

* * * * *